Feb. 16, 1965 J. R. MITTLEIDER Plant Pat. 2,478
DIANTHUS PLANT
Filed Sept. 23, 1963
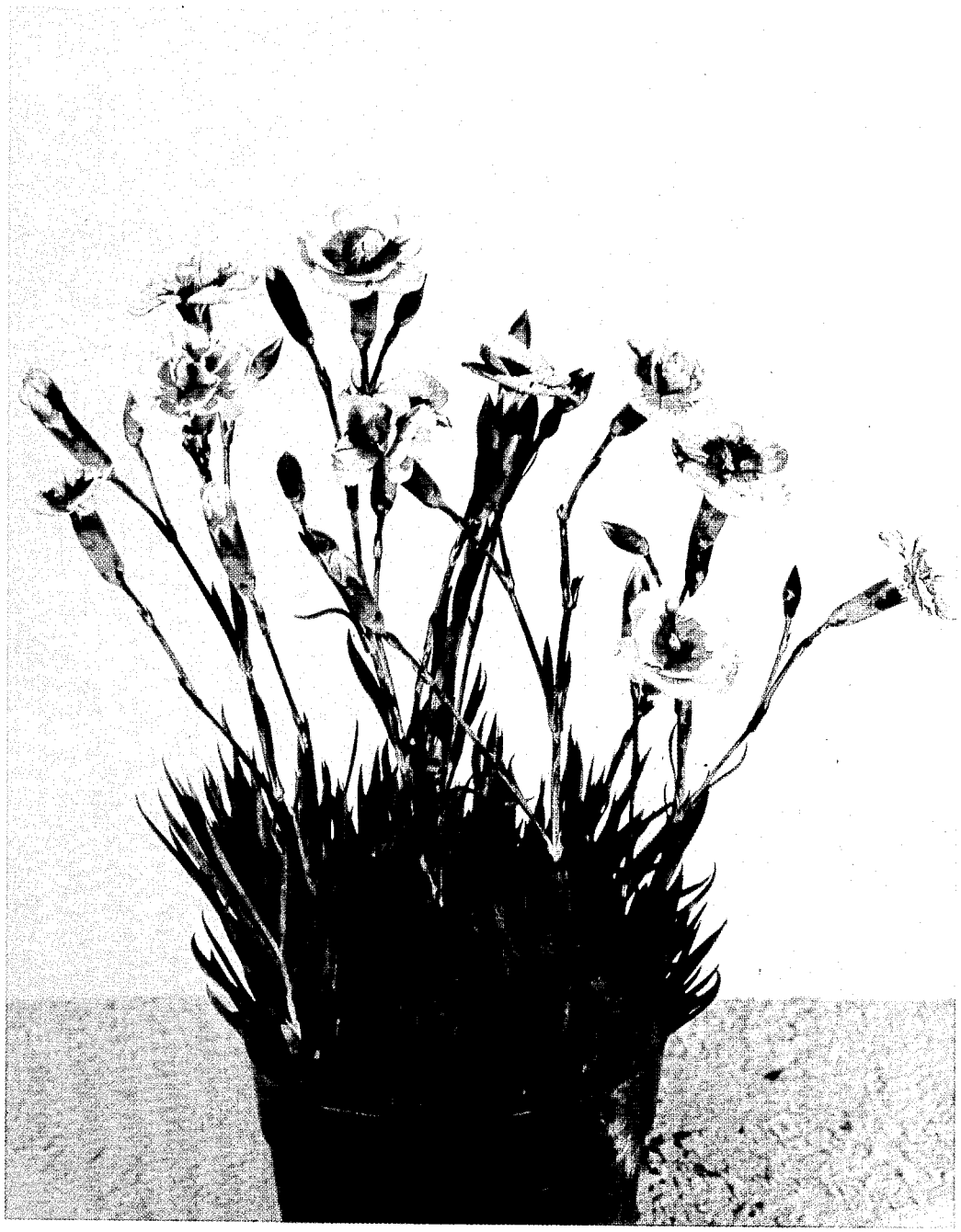
INVENTOR
JACOB R. MITTLEIDER
By Herbert E. Kidder
AGENT United States Patent Office Plant Pat. 2,478

Patented Feb. 16, 1965

2,478

DIANTHUS PLANT

Jacob R. Mittleider, Loma Linda, Calif., assignor to Milo Academy, Inc., Milo, Oreg., a corporation of Oregon Filed Sept. 23, 1963, Ser. No. 310,962
1 Claim. (Cl. Plt.—70)

The present invention relates to a new and distinct variety of dianthus plant, which is characterized particularly by a low growing, compact, densely tufted plant bearing numerous large, duplex, parti-colored flowers shading abruptly from dark magenta centers to light rosy pink margins, said flowers being borne at the ends of 8 to 10 inch stems and having a very faint carnation-like fragrance.

The new and different plant variety is the result of an extensive breeding program at my nursery in Loma Linda, California, seeking new varieties of dianthus that would be especially suitable for mass plantings or edgings, without the necessity of staking the blooms. The characteristics sought were: (1) carnation foliage; (2) ever-blooming habit; (3) compactness; (4) fragrance; (5) large blooms; (6) strong stems; (7) hardiness and disease resistance; (8) pleasing new colors.

The present variety is the result of a three-step breeding process, in which the first step consisted in pollinating a Dianthus Ruby Gem (unpatented) with pollen from a seedling of the Malmaison strain of carnations. The Malmaison strain of carnations is characterized chiefly by its large blossoms, and is used primarily for breeding purposes. The Malmaison used in this first cross had flowers of smoky blue-white. Pollen from seedlings resulting from this first cross was then used to pollinate Dianthus Wallace Red, an unpatented *plumarius* hybrid. Seedlings from this second cross were then "selfed," which is a term for artificially pollinating plants within a group having the same genes. The present variety was discovered among some 15,000 seedlings resulting from this third step.

The original reproduction of the plant by cuttings was carried out in the experimental section of my nursery at Loma Linda, California.

Asexual reproduction of my new variety by cuttings, as performed by me at the nursery, shows that the characteristics and distinctions of the variety come true to form and are established and transmitted through succeeding propagations.

The plant grows best in well-drained, loamy soil, but is not critical as to the pH of the soil. Best blooms are obtained when the plant is grown in full sunlight.

The accompanying drawing shows a typical plant of my new variety, showing the flowers and foliage depicted in color as nearly true as it is reasonably possible to make the same in a color illustration of this character.

The following is a detailed description of my new variety, as based on my observations of specimens grown at Loma Linda, California, with color terminology and identifications in accordance with "A Dictionary of Color" by Maerz and Paul.

Plant:

*Form.*—Compact, growing to a height of two to three inches.

*Growing habit.*—Densely tufted.

*Blooming habit.*—Floriferous, flowering evenly over the entire plant, with many blossoms ranging from 1¾ inches in diameter to 2 inches, and ranging in number from 3 or 4 on a one year old plant grown in three inch pots, up to 20 or more on two year old plants.

*Blooming season.*—Perpetual in southern California, or wherever the mean temperature is above 50° F. Where the mean temperature drops below 50° F., the plant becomes dormant and ceases to bloom. Maximum bloom in southern California occurs from March through July, and in October and November; while minimum bloom occurs from August to October and from December through February.

*Foliage size.*—Maximum size of mature leaves on thrifty young plants is approximately 2 to 3 inches in length, by three-sixteenths of an inch in width.

*Quantity.*—Abundant.

*Shape.*—Lanceolate, or grass-like.

*Color.*—Growing under good conditions, the color of mature leaves is a deep true green corresponding almost exactly to Aspen Green (Plate 31–C–6 in Maerz and Paul's Color Dictionary).

*Texture.*—Glaucous.

Flower:

*Size.*—The maximum size is about 1¾ to 2 inches in diameter, by about ⅝ inch high.

*Borne.*—At the end of the stem.

*Stem.*—Stiff and upright, approximately 8 to 10 inches in length.

*Petalage.*—Duplex.

*Color.*—The flower is parti-colored, with magenta colored centers (Plate 52–L–9, Maerz and Paul) shading abruptly to light, rosy pink margins (Plate 2–A–3, Maerz and Paul).

*Petals.*—Firm in texture, of obovate form, with slightly crenate or acuminate margins. The size of the individual petals is about 1 inch in length by ¾ inch in width.

*Fragrance.*—Very faint, carnation-like.

*Calyx.*—Almost cylindrical, very slightly tapered, with acuminate teeth, and approximately 1 inch in length.

Compared to other well-known dianthus plants, this new variety is distinguished by its low-growing, compact form and distinctive, parti-colored, duplex flowers with magenta centers shading abruptly into light rose pink margins, borne at the ends of 8 to 10 inch long stems, and having a very faint, carnation-like fragrance.

I claim:

A new and distinct variety of dianthus plant, substantially as shown and described herein, characterized particularly by its floriferous blooming habit, low-growing, compact, densely tufted plant form usually not exceeding two to three inches in height, and bearing many duplex, parti-colored flowers having magenta centers and shading abruptly into light rosy pink margins, said flowers having a very faint carnation-like fragrance, and being borne on the ends of stiff, upright stems of approximately 8 to 10 inches in height.

No references cited.